United States Patent [19]

MacConnell

[11] Patent Number: 5,139,637

[45] Date of Patent: Aug. 18, 1992

[54] PLASMID PURIFICATION SYSTEM AND METHOD

[76] Inventor: William P. MacConnell, 1849 Rubenstein Dr., Cardiff, Calif. 92007

[21] Appl. No.: 668,856

[22] Filed: Mar. 13, 1991

[51] Int. Cl.⁵ .................. G01N 27/26; G01N 27/447; B01D 57/02

[52] U.S. Cl. .................. 204/299 R; 204/182.8; 204/301

[58] Field of Search .............. 204/182.8, 182.1, 182.7, 204/182.9, 299 R, 301

[56] References Cited

U.S. PATENT DOCUMENTS

| | | | |
|---|---|---|---|
| 3,255,100 | 6/1966 | Raymond | 204/182.1 |
| 3,533,933 | 10/1970 | Strauch | 204/180 |
| 3,616,454 | 10/1971 | Levy et al. | 204/299 |
| 3,640,813 | 2/1972 | Nerenberg | 204/299 |
| 3,715,295 | 2/1973 | Tocci | 204/180 G |
| 3,755,121 | 8/1973 | Schlutz | 204/180 G |
| 3,902,986 | 9/1975 | Nees | 204/299 R |
| 3,951,776 | 4/1976 | Eibl et al. | 204/299 R |
| 3,969,218 | 7/1976 | Scott | 204/299 R |
| 3,989,612 | 11/1976 | Kragt et al. | 204/182.8 X |
| 4,049,534 | 9/1977 | Posner | 204/299 R |
| 4,159,933 | 7/1979 | Allington | 204/299 R X |
| 4,164,464 | 8/1979 | Allington | 204/299 R |
| 4,443,319 | 4/1984 | Chait et al. | 204/299 R |
| 4,576,702 | 3/1986 | Peck et al. | 204/299 R |
| 4,576,703 | 3/1986 | Peck et al. | 204/299 R |
| 4,608,146 | 8/1986 | Penaluna | 204/299 R |
| 4,634,513 | 1/1987 | Asao | 204/182.8 X |
| 4,699,706 | 10/1987 | Burd et al. | |
| 4,707,233 | 11/1987 | Margolis | 204/182.3 |
| 4,725,348 | 2/1988 | Diekmann | 204/299 R |
| 4,747,918 | 5/1988 | Wassenberg, II | 204/182.8 |
| 4,824,547 | 4/1989 | Zhang et al. | 204/299 R |
| 4,859,302 | 8/1989 | Alfenito | 204/182.8 |
| 5,102,518 | 4/1992 | Doering et al. | 204/182.8 X |

*Primary Examiner*—John Niebling
*Assistant Examiner*—John S. Starsiak, Jr.
*Attorney, Agent, or Firm*—Baker, Maxham, Jester & Meador

[57] ABSTRACT

An apparatus for the purification of DNA and the like comprises a housing having walls forming a reservoir having a plurality of chambers for containing a buffer solution means for circulating a buffer through the reservoir, a disposable cassette within said housing having first means including a gel for defining a first path extending between a first pair of the chambers, a well for introducing a bacterial sample into the path at one end thereof, and a second path intersecting the first path via an elution window at one end, having a collection window at the other end and extending between a second pair of the chambers, and an electrical circuit for selectively applying an electrical potential along each of the paths for selectively moving a plasmid first along the first path from the bacterial well to the elution window, then along the second path to the collection window at the end thereof.

20 Claims, 2 Drawing Sheets

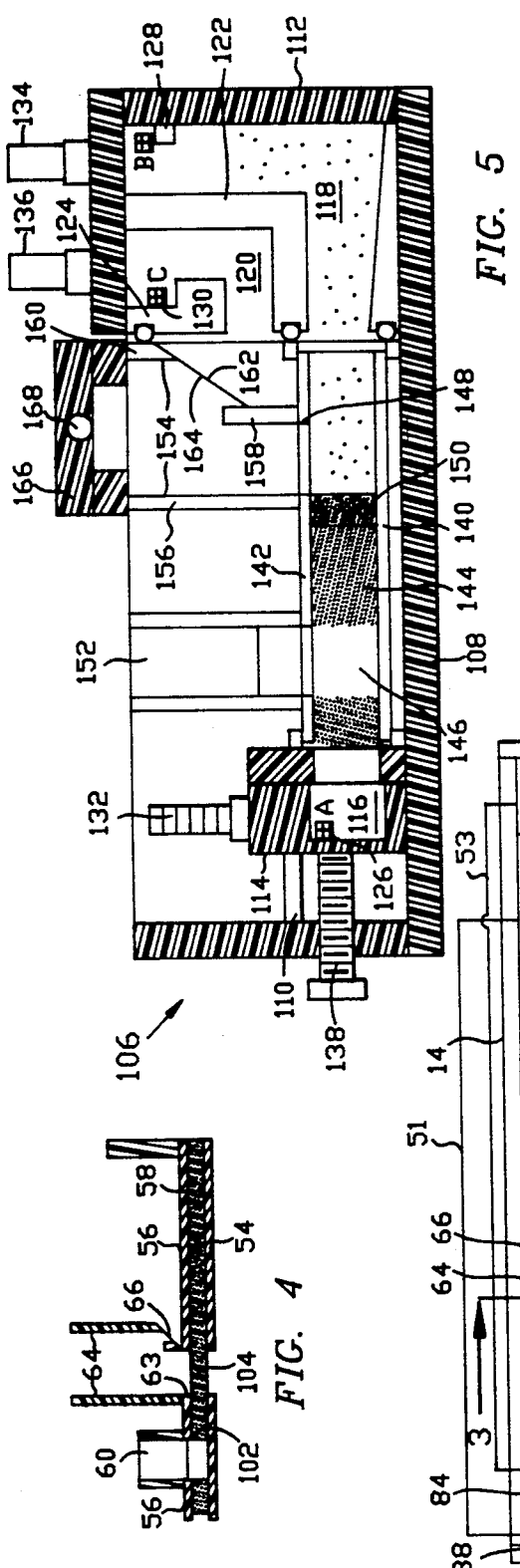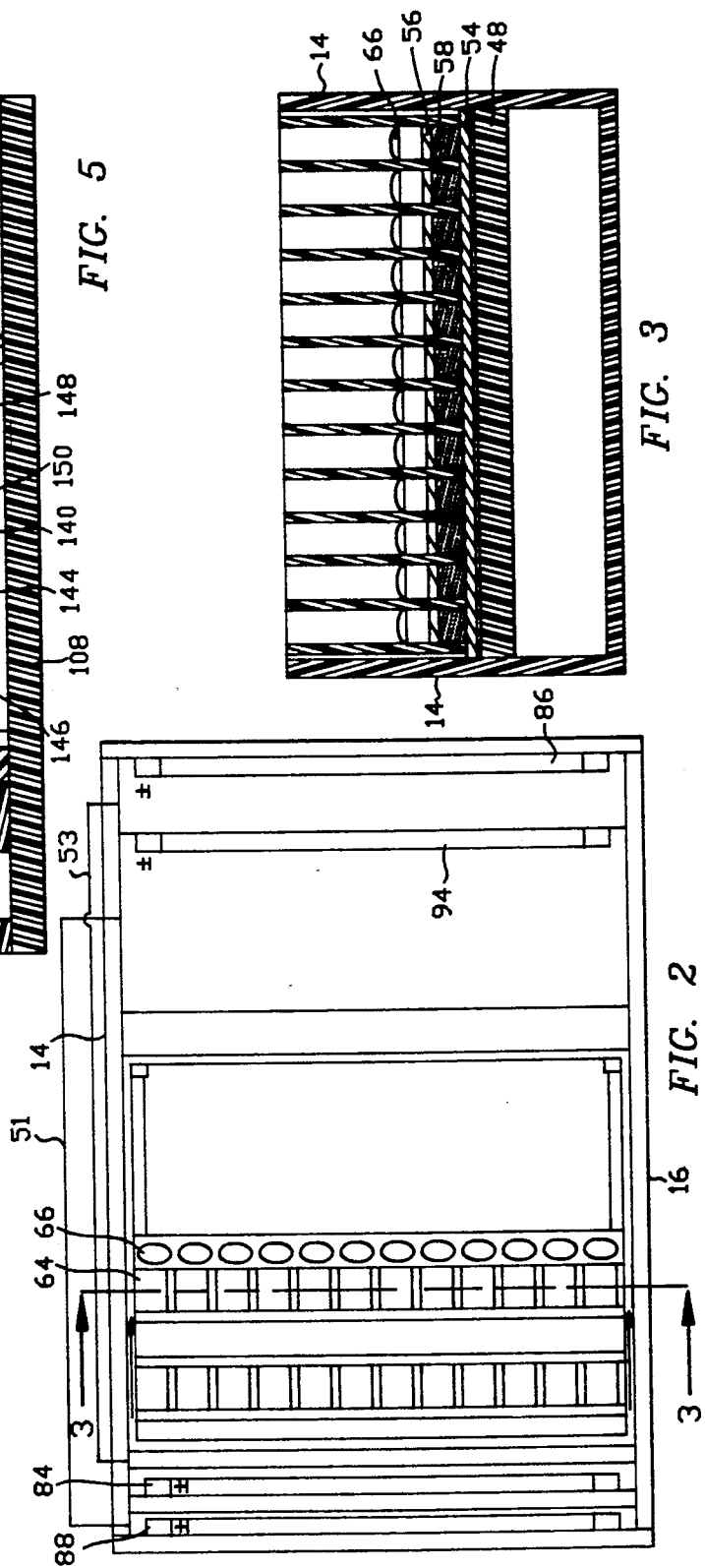

PLASMID PURIFICATION SYSTEM AND METHOD

BACKGROUND OF THE INVENTION

The present invention relates to the purification of plasmids and pertains particularly to an improved method and apparatus for the purification of plasmids and the like.

A great deal of laboratory research is carried out in which recombinant DNA techniques are utilized. Among the research activities carried out are DNA sequencing, DNA restriction mapping, DNA probe generation, construction of other plasmid or related DNA from smaller pieces, RNA transcription from a plasmid template, hybridization blot analysis, transformation into bacterial, yeast or mammalian cells, S1 nuclease mapping, microinjection into embryos, and election microscopy analysis. All of these require substantially pure concentrations of plasmid DNA.

Many techniques and apparatus exist for small scale purification of plasmid DNA. The typical prior art approach to the purification of plasmids involves a series of steps, including a collection of cells grown in liquid culture by centrifugation, separation of the bacterial chromatic (genomic) DNA, and cellular debris from the soluble contents of the bacteria by centrifugation of filtration, and concentration of the plasmid DNA apart from other cellular components by alcohol or isopropanol, absorption to solid media (i.e. ion exchange resin, glass powder, reverse phase chromatography resin, etc.), or salt precipitation. Additional purification steps may be added to these, such as phenol/-chloroform extraction, secondary alcohol precipitation, protease or ribonuclease treatment to further purify the plasmid DNA.

Other methods of plasmid purification include the additional steps of the addition of CsCl to supernatnat from the bacterial lysis after removal of the bacterial genomic DNA, followed by ultracentrifugation. The ultracentrifugation results in a CsCl density gradient in which the plasmid DNA forms a sharp band. This band is removed from the gradient and the DNA separated from the CsCl by alcohol precipitation or other suitable means. These procedures are widely used in molecular biology research for plasmid purification, and have been refined to produce plasmid DNA which is suitable for use in virtually any subsequent procedure of molecular biology.

Certain apparatus have been developed for purification of plasmid DNA. One such apparatus is available from a company called Applied Biosystems, and can purify DNA from samples of tissue, blood, bacteria, etc. The apparatus utilizes repeated organic extraction of sample material to release and purify the DNA. Reagents drawn from reservoirs are automatically introduced into sample containing vials in which the aqueous/organic extraction occurs. Either phenol or guanidine isothiocynate can be used by the machine as the organic phase material. After the extraction steps, the DNA is concentrated on chromatography resin, which is held in the upper portion of the extraction vials. The operator then removes the vials from the instrument and elutes the DNA manually from the resin. This apparatus is designed primarily for purification of genomic DNA from mamalian cells, tissue, blood, etc. and does not perform well with bacterial plasmid DNA. The machine has no capability of separating the plasmid from bacterial DNA.

A fully automated machine is available from Autogen, Inc., which is designed to purity plasmid DNA from recombinant bacteria. This machine is essentially an electronically controlled mechanical robot which performs multiple small scale plasmid purifications. The machine utilizes a precision centrifuge, with sets of disposable plastic tubes into which starting bacterial cultures are placed. Robotic pipet holders positioned above the centrifuge introduce and remove fluids from disposable sample tubes during the run, which involves centrifugation of the samples at two different steps or cycles. This machine can purify up to twelve samples of plasmid DNA in less than an hour. However, the machine is extremely expensive for laboratory use.

Other techniques for separation of substance include electrophoresis separation. Exemplary of this approach are the following U.S. Patents:

Strauch, U.S. Pat. No. 3,533,933, granted Oct. 13, 1970, entitled, "Process and Device for the Isolation of Fractions of a Substance Mixture Electrophoretically Separated in a Carrier Gel", discloses a vertical separation column which is filled partially or completely with a carrier gel with an elution chamber at the bottom of the column.

Levy, U.S. Pat. No. 3,616,454, granted Oct. 26, 1971, entitled "Method of an Apparatus for Electrophoretic Separation in a Gel Column", discloses an apparatus wherein a specimen is placed in the upper end of a polyacrylamide gel column of an electrophoresis whose lower end terminates at a receptacle containing an elution solution.

Nerenberg, U.S. Pat. No. 3,640,813, granted Feb. 8, 1972, entitled "Adapter for a Macromolecule Separation Device", discloses a gel medium disposed in a vertical column with an adapter for the lower end of the column containing a gel and channels for fluid ingress to the upper gel surface and egress therefrom.

The following patents are of interest in disclosing related methods and apparatus:
U.S. Pat. No. 3,579,433, granted May 18, 1971;
U.S. Pat. No. 3,715,295, granted Feb. 6, 1973;
U.S. Pat. No. 3,755,121, granted Aug. 28, 1973;
U.S. Pat. No. 3,951,776, granted Apr. 20, 1976; and
U.S. Pat. No. 4,164,464, granted Aug. 14, 1979.

Many of these existing methods and apparatus have a number of drawbacks, and are generally unsatisfactory in that they are expensive and require many complicated steps and procedures. Others are unable to produce satisfactory purity and quantities.

It is desirable that a simple, inexpensive, yet reliable method and apparatus be available for purification of plasmid DNA starting directly from bacterial culture or collected bacterial cells.

SUMMARY AND OBJECTS OF THE INVENTION

It is the primary object of the present invention to provide an improved method and apparatus for the purification of plasmids and the like.

In accordance with a primary aspect of the present invention, an apparatus for the purification of DNA and the like comprises a housing forming a reservoir having a plurality of chambers for containing a buffer solution, means for circulating a buffer through said reservoir, disposable means positionable within said housing, and having first means including a gel for defining a first path extending between a first pair of said chambers, means for introducing a bacterial sample into said path at one end thereof, and second means for defining a second path intersecting said first path via an elution window at one end, having a collection window at the other end and extending between a second pair of said chambers, and means for selectively applying an electrical potential along each of said paths for selectively moving a plasmid first along said first path from said bacterial sample to the intersection of said first path, then along said second path to said collection window at the end thereof.

BRIEF DESCRIPTION OF THE DRAWING

The above and other objects and advantages of the present invention will become apparent from the following description when read in conjunction with the accompanying drawings wherein:

FIG. 2 is a top plan view of the embodiment of FIG. 1;

FIG. 3 is a section view taken on line 3—3 of FIG. 2;

FIG. 4 is a side elevation view of an alternate embodiment of the disposable cassette; and FIG. 5 is an alternate embodiment of the invention.

DETAILED DESCRIPTION OF PREFERRED EMBODIMENTS

Figure 1:
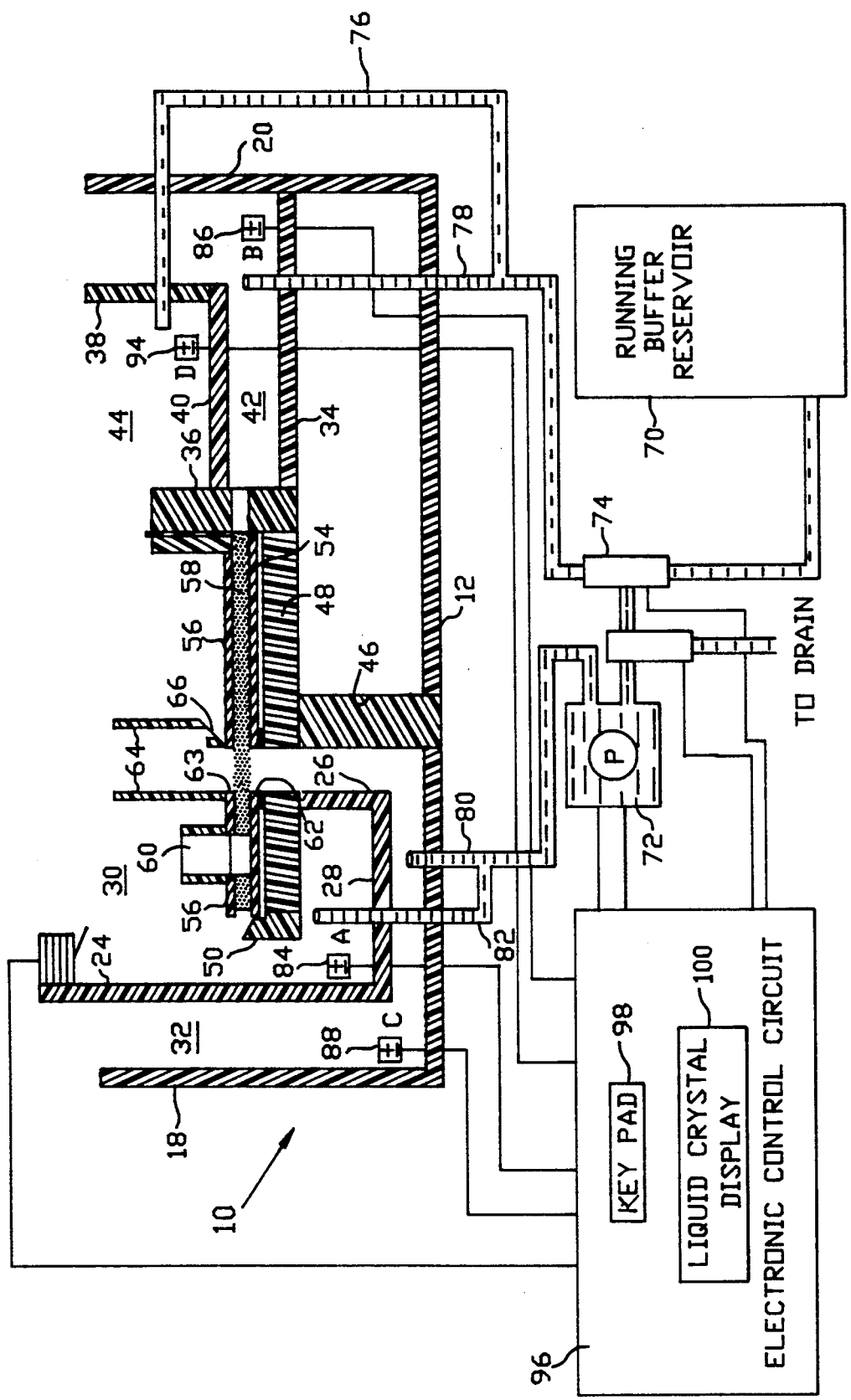
FIG. 1 is a side elevation view of a preferred embodiment of the invention.

Referring to the drawing, and particularly to FIGS. 1-3, there is illustrated a system in accordance with a preferred embodiment of the present invention, designated generally by the numeral 10. The system comprises a primary or outer housing having a generally box-like configuration, with a bottom wall 12, opposed side walls 14 and 16, and opposed end walls 18 and 20 forming a generally open top box-like housing. The housing is provided with inner walls or partitions dividing it into a multiple of at least two pairs of chambers or reservoirs. As best seen in FIG. 1, at the left hand side thereof, a pair of vertical walls 24 and 26 join with a horizontal bottom wall 28 spaced upward from the bottom wall 12, forming a first reservoir 30 of a first pair of reservoirs, and a second reservoir 32 of a second pair of reservoirs.

At the other or right hand end of the housing, a second reservoir of the first pair is formed by a horizontally extending wall 34 and a vertical wall or partition 36. A second vertical wall 38 and a horizontal wall 40 form second reservoirs 42 and 44, respectively, of the previously mentioned reservoirs. The reservoirs 30 and 42 form a first pair of reservoirs, and the reservoirs 32 and 44 form a second pair of reservoirs for containing a running buffer fluid as will be described. Circulation lines on conduits 51 and 53 are provided between the chambers of each pair.

Disposed between the pairs of reservoirs is a holding or mounting structure for mounting a disposable cassette, which provides communication between the pairs of chambers. This mounting structure includes a vertical support wall 46 on top of which rests a horizontal support table or member 48 connected to vertical wall 36 at one end, and a vertically extending abutment structure 50 on the other end. A disposable cassette is detachably or releaseably mounted in this support structure between wall 36 and abutment 50.

The cassette generally comprises a pair of vertically spaced apart bottom and top panels 54 and 56, with a body of suitable gel, such as agarose gel 58 sandwiched therebetween and exposed at both ends to chambers 30 and 42. Other suitable gels may be used in place of agarose, such as starch, gelatin or cross-linked versions of agarose, polyacrylamide, starch, or gelatin. Another agarose substitute is available under the trademark Synergel from Diversified Biotech, 46 Marcellus Drive, Newton Centre, MA. The gel should have a vertical thickness of about three to five tenths (0.20–0.50) inch. The body of gel is exposed via a window 62 with chamber 32, and a window 63 with a microchamber 64, and via a dialysis window 66 with chamber 44. A plurality of spacer walls are disposed between the panels 54 and 56 dividing the space therebetween into a plurality of channels that extend from one end (the inlet wells) to the other for containing an agarose gel, as will be described. Thus, multiple paths (twelve illustrated) extend between the pairs of chambers.

Referring to FIGS. 2 and 3, a plurality of sample wells each communicating with each of the aforementioned paths are formed at 64 for receiving samples or charges containing DNA. A plurality of separate elution windows each communicating with the aforementioned paths intersect the upper and lower walls of the cassette downstream of the sample wells, and each communicate with a microchamber at the upper surface thereof. The distance from the wells 60 to the elution windows is on the order of from about four tenths (0.40) to about one and two tenths (1.2) inches, but could be a little longer if the times of electrophoresis were lengthened. This distance is important to the resolution capabilities of the separation medium.

The microchambers are each provided with a window cell, each comprising an opening covered by a dialysis membrane extending at about a forty-five degree angle to the horizontal. Each of these window cells form a collection cavity at least partially around each window. A suitable dialysis membrane is available from Spectrum, 1100 Rankin Road, Houston, Texas. These are available in varying molecular weight range. The membrane may be secured to cover the holes by a suitable bonding agent, such as "Super Glue-5" manufactured by Loctite Corporation, Cleveland, Ohio. The window should have a minimum diameter of about one-quarter (0.25) inch. In this embodiment, an agarose gel is disposed in the channels between the upper wall 56 and lower wall 54 to provide a path for the electrophoresis of the plasmid DNA. This cassette detachably mounts as shown within the holder of the housing.

Referring to FIGS. 1 and 2, a source of buffer fluid, such as a reservoir 70, supplies a buffer fluid which is circulated through the chambers by way of a pumping system, including a pump 72 for supplying buffer fluid by way of a plurality of three-way solenoid valves 74 and conduits to the respective reservoirs. The system is set up to circulate the buffer fluid to maintain and control the pH thereof and to aid in the control of the temperature.

The pairs of chambers or reservoirs are provided with opposing electrodes, with a pair of opposing electrodes 84 and 86 in chambers 30 and 42, and a pair of electrodes 88 and 94 disposable respectively in the chambers 32 and 44. These electrodes are connected through an electronic control system or circuit 96, preferably having a CPU with controls through a keypad 98 and a suitable display 100.

In operation, the electrophoresis chambers and cassette microchamber are filled with a running buffer.

The wells 60 are then loaded with up to 1.0 milliliter of bacterial culture mixed with one-seventh volume of lysis buffer. On example of a lysis buffer comprises 50% glycerol, 1% (W/V) SDS, 25 mM EDTA, and 25 mM Tris-HCL pH 7.5). The viscus lysed bacterial culture is then loaded in the separate wells or slots of the cassette.

A DC current is applied to the electrodes 84 and 86, which causes the separation of the solubilized bacterial components into unique portions of the gel with the DNA at the elution windows. During the separation, direct current voltage is applied to the gel, first in a discrete amount, preferably 50 volts for 15 minutes, followed by 100 volts for 15 minutes, followed by 150 volts for 20-50 minutes. Increasing the voltage over time allows for better separation of large and small bacterial components. The gradual voltage increase, as described above, prevents an excess heat build up. Once the plasmid DNA separation has occurred in the separation gel, electrodes 84 and 86 are then deactivated and electrodes 88 and 94 are then activated. This causes the plasmid DNA located in the gel window region to electroelute out of the separate gel lanes and into their corresponding microchamber compartments, which are filled with a running buffer. The electrode 94 attracts the negatively charged DNA toward itself, which forces the DNA to move through the microchamber buffer and concentrate against the dialysis membrane windows 66.

Once the plasmid DNA is concentrated against the microchamber window, the buffer contained in the microchamber block is manually removed with a pipet, which leaves a small volume of buffer remaining in the window cell of the microchamber block. This buffer, which ranges in volume from 10 to 40 microliters, contains the purified plasmid DNA. The current to electrodes 88 and 94 are disconnected, and the buffer in the window cell 66 is manually pipetted up an down two to three times by the operator to stir the DNA off the dialysis membrane and into the buffer. The resulting DNA is highly pure and concentrated in the electrophoresis running buffer, in which it is stable for storage.

A further improvement in the above apparatus and method involves substituting an agarose-acrylamide double phase gel in place of the one percent agarose gel in the disposable cassette. Referring to FIG. 4, the double phase agarose-acrylamide gel cassette is illustrated wherein like numbers represent like elements. The cassette in this embodiment is identical to the prior embodiment, except the gel path is a two phase path, with an initial one percent agarose portion 102 and a second five percent acrylamide or acrylamide-like substitute portion 104. The substance polyacrylamide is made up of acrylamide and bis-acrylamide polymerized in various combinations. Other acrylamide-like substances can be used in place of acrylamide, such as "Hydrolink", trademark, from the company AT Biochem, 4 Great Valley Parkway, Malvern, PA, 19355, or "istacryl" from the company Eastman Kodak, Ranway, New Jersey. The above acrylamide/bis-acrylamide and acrylamide-like substances are hereafter referred to as acrylamide. The agarose portion extends up to a position just short of the elution window 63, where the five percent acrylamide portion begins and extends past the elution window.

When a one percent agarose is used, low molecular weight ionically charged materials may co-elute with the plasmid DNA during the electroelution stage. These materials concentrate against the dialysis membrane with the plasmid DNA. Various types of agarose have been tried which contain less of these elutable materials. Agaroses from FMC Inc, GTG(P) and GTG type have proven to yield the least amount of these materials, but still are not devoid of them.

The agarose-acrylamide double phase gel is employed, wherein the plasmid DNA first separates in the agarose 102, then passes into a five percent acrylamide gel 104, which begins directly under the elution window, interfacing the agarose and continuing to fill the remainder of the rear portion of the cassette. Once the DNA moves into the acrylamide phase, the lower molecular weight components from the agarose pass in front of the DNA and away from the elution window. The DNA is then eluted as before into the microchamber and the dialysis membrane. This separates and further purifies the DNA.

Referring now to FIG. 5, an alternate embodiment is illustrated wherein one of the buffer chambers is alternately paired with two other chambers during the purification process. Thus, the two pairs of chambers share a common chamber. The apparatus, designated generally by the numeral 106, comprises a generally rectangular open top box-like housing having a bottom 108, with the end walls 110 and 112 and side walls not shown. A movable generally C-shaped wall 114 at one end of the housing forms a chamber 116 and communicates by way of a disposable cassette, as will be described, with a pair of chambers 118 and 120 at the other end of the housing. The chambers 118 and 120 are formed by the walls and bottoms of the main housing, together with interior partitions 122 and 124. An electrode 126 located in chamber 116 is selectively paired with electrode 128 in chamber 118, and with electrode 130 in chamber 120 for carrying out the process. A buffer fluid is flowed around the electrodes by way of inlet ports 132 to chamber 116 and electrode 126, inlet 168 to cassette microchamber leading to chamber 118, and electrode 128 and inlet 136 to chamber 120 and electrode 130. Outlet ports (not shown) exist for chambers 116 and 120. The buffer may be circulated as in the previous embodiment or contain a flowthrough arrangement, such that impurities may be removed from the buffer fluid during the process.

The wall 114 is moved by means of a hand screw 138 to move it toward and away from wall 110 into and out of clamping engagement with a removable cassette, which forms paths as in the previous embodiment between pairs of chambers within the apparatus containing a buffer. The cassette comprises a bottom horizontally extending wall or panel 140 and an upper horizontally extending wall or panel 142, which may be connected together by spaced partitions as in the previous embodiment for forming a plurality of paths or channels. An agarose gel 144 extends along from the inlet end of the cassette and containing an inlet cavity or well 146 to a position just short of an elution window 148. The one percent agarose gel 144 abuts and interfaces with a five percent acrylamide up to the elution window 148. A plurality of upwardly extending inlet wells 152 communicate with the inlet cavity or well 146 within the agarose gel.

The left hand end of the cassette communicates with chamber 116, and the right hand chamber opens directly and communicates directly with chamber 118. The elution window 148 communicates with a microchamber 154 formed by upstanding walls 156 and dialysis membrane 162 extending at an angle of on the order of about forty-five degrees, forming a plasmid collection cavity and window 164. A cover 166 over the top of the microchamber 154 includes an inlet port 168 for the introduction of a buffer into the microchamber.

The apparatus functions much the same as in the previous embodiment wherein lysed bacteria are loaded into the well 146, buffer is loaded into the respective chambers and/or circulated therethrough, and an electrical potential is imposed across electrodes 126 and 128. The electrophoresis forces the DNA to move from the direction of the electrode 126 toward the electrode 128 along the gel 144. After an appropriate length of time, the DNA has moved into the section of acrylamide 150, while impurities have moved into the buffer at the end of the cassette and into the chamber 118. As the impurities have been separated from the DNA as it is moved into the acrylamide, the electrode 128 is deactivated and the electrode 130 is activated. The flow to inlet 168 is stopped, while maintaining the flow to inlets 132 and 136. This imposes an electrical potential between electrodes 126 and 130, causing the DNA to elute out through the window and into the microchamber 154 where it collects on the membrane 162 in the collection cell 164. The buffer is then drained from the chambers, and the DNA collected as in the previous embodiment.

Experiments have been carried out with the apparatus and the results have proven satisfactory. By way of example, one experiment was carried out by the following steps in an embodiment according with FIG. 1:

1. E. coli strain DH5aF' (BRL Inc.) containing a 3.0 kilobase pair plasmid (Stratagene Inc., Bluescript) was grown overnight in L-broth with ampicillin antibiotic.

2. 300 microliters of this bacteria was lysed in separate tubes with 40, 50, 60 microliters of lysis buffer (lysis buffer: 50% glycerol, 1% (W/V) SDS, 25 mM EDTA, and 25 mM Tris-HCL pH 7.5).

3. A prototype cassette as illustrated in FIG. 2A was loaded with 1% agarose gel (made up in running buffer: 0.02 M Tris Acetate, 0.001 M EDTA pH 8.0). The very beginning portion of the agarose gel was impregnated with ribonuclease (RNase) which was devoid of DNase activity.

4. The prototype instrument was filled with running buffer (0.02 M Tris Acetate, 0.001 M EDTA pH 8.0).

5. The above sample along with purified plasmid DNA as a control was loaded into separate wells of the sample cassette. The microchamber block of the cassette was filled with running buffer.

6. Recirculation of the running buffer between the + and − electrode chambers was begun, the flow rate was approximately 100 ml/minute.

7. 50 volts of direct current was applied to electrodes A(−) and B(+) for two hours while recirculation was occurring. (see FIG. 2)

8. Electrodes A and B were disconnected and 70 volts of direct current was applied to electrodes C(−) and D(+) for 2 hours to electroelute the DNA into the window cells of the microchamber block.

9. The microchamber block was drained by manually pipetting the buffer out of each microchamber.

10. The DNA sample from each appropriate microchamber window cells was pipetted up and down 3 times and transferred out of the microchambers into eppendorf tubes.

11. The DNAs were then run on a 1% neutral agarose gel and the DNA band were stained with ethidum bromide to determine the approximate purity and yield of the DNAs. Purified plasmid DNA were run along beside the above as a standard.

12. Samples of the DNA were used for DNA sequencing and were cut with restriction enzymes to determine if the DNA was suitable for those procedures.

Analysis of the DNA obtained from the above procedure resolved on 1% agarose gels (stained with ethidium bromide) revealed that the plasmid DNA was highly purified. The only ethidium bromide stainable components visible in these gels was the plasmid DNA. Further, the purified DNA was used as the template for DNA sequencing using the dideoxy sequencing protocol which resulted in clear, readable sequence data.

The invention herein is also applicable for purification of other kinds of DNA, including but not limited to M13 phage DNA or lambda phage DNA.

While I have illustrated and described my invention by means of specific embodiments, it should be understood that numerous changes and modifications may be made therein without departing from the spirit and scope of the invention as defined in the appended claims. I further assert and sincerely believe that the above specification together with the accompanying drawings contains a written description of the invention and the manner and process of making and using it, in such full, clear, concise, and exact terms as to enable any person skilled in the art to which it pertains, or with which it is most nearly concerned, to make and use the same, and further that it sets forth the best mode contemplated by me for carrying out the invention.

I claim:

1. An apparatus for the purification of DNA and the like comprising:

a housing forming a reservoir having a plurality of chambers for containing a buffer solution;

means for circulating a buffer through said reservoir;

disposable means positionable within said housing and having first means including a gel for defining a first path extending between a first pair of said chambers, means for introducing a bacterial sample into said path at one end thereof, and second means for defining a second path intersecting said first path via an elution window at one end, having a collection window at the other end and extending between a second pair of said chambers; and means for selectively applying an electrical potential along each of said paths for selectively moving a plasmid first along said first path from said bacterial sample to the intersection of said first path then along said second path to said collection window at the end thereof.

2. A purification apparatus according to claim 1 wherein said gel is an electrophoretic agarose gel.

3. A purification apparatus according to claim 1 wherein said gel is an agarose-acrylamide double phase gel.

4. A purification apparatus according to claim 3 wherein said gel has an approximate one percent agarose phase extending from said inlet means part way to said elution window, and an approximate five percent acrylamide phase extending from said agarose phase to said elution window.

5. A purification apparatus according to claim 1 wherein said disposable means comprises a body formed of a non-conductive material with upper and lower spaced apart panels for containing said gel and defining said first path, wall means extending upward from around a window in said upper panel for defining said inlet means, upstanding walls surrounding said elution window for defining at least part of said second path, and said collection window comprises a membrane covering an opening in said upstanding walls.

6. A purification apparatus according to claim 5 wherein gel is an electrophoretic agarose gel.

7. A purification apparatus according to claim 5 wherein said gel is an agarose-acrylamide double phase gel.

8. A purification apparatus according to claim 7 wherein said gel has an approximate one percent agarose phase extending from said inlet means part way to said elution window, and an approximate five percent acrylamide phase extending from said agarose phase to said elution window.

9. A purification apparatus according to claim 5 wherein said disposable body is formed of a plurality of said first paths and a plurality of said second paths.

10. A purification apparatus according to claim 5 wherein said membrane of said collection window comprises a dialysis membrane extending at an angle of approximately forty-five degrees to the horizon, disposable body is formed of a plurality of said first paths and a plurality of said second paths.

11. An apparatus for the purification of DNA and the like comprising:
    a generally box-like housing forming a reservoir having a plurality of chambers for containing a buffer solution;
    means for circulating a buffer through said reservoir;
    a disposable cassette detachably mountable within said housing and having a pair of vertically spaced horizontally extending walls, including an electrophoretic agarose gel disposed therebetween for defining at least a part of a first path extending generally horizontally between a first pair of said chambers, an inlet well for introducing a bacterial sample into said path at one end thereof, and vertically aligned openings in said walls defining an elution window, a microchamber having a collection window and communicating with said elution window for defining a second path intersecting said first path via said elution window and extending between a second pair of said chambers; and
    means for selectively applying an electrical potential along each of said paths for selectively moving a plasmid first along said first path from said inlet well to said elution window, then along said second path to said collection window at the end thereof.

12. A purification apparatus according to claim 11 wherein said disposable cassette comprises a body formed of a non-conductive material wherein said walls comprise upper and lower spaced apart panels for containing said gel and defining said first path, wall means extending upward from around a window in said upper panel for defining said inlet well, upstanding walls surrounding said elution window for defining at least part of said second path, and said collection window comprises a dialysis membrane covering an opening in said upstanding walls.

13. A purification apparatus according to claim 12 wherein said gel is an agarose-acrylamide double phase gel.

14. A purification apparatus according to claim 13 wherein said gel has an approximate one percent agarose phase extending from said inlet means part way to said elution window, and an approximate five percent acrylamide phase extending from said agarose phase to said elution window.

15. A purification apparatus according to claim 12 wherein said disposable cassette includes a plurality of vertically extending walls disposed between said vertically spaced horizontally extending walls forming a plurality of said first paths and a plurality of said second paths.

16. A purification apparatus according to claim 12 wherein said membrane of said collection window comprises a dialysis membrane extending at an angle of approximately forty-five degrees to the horizon.

17. A process for the purification of DNA and the like comprising the steps of:
    selecting a housing having walls forming a reservoir having a plurality of chambers for containing a buffer solution;
    circulating a buffer through said reservoir;
    selecting and positioning disposable means within said housing and having first means including a gel for defining a first path extending between a first pair of said chambers, means for introducing a bacterial sample into said path at one end thereof, and second means for defining a second path intersecting said first path via an elution window at one end, having a collection window at the other end and extending between a second pair of said chambers;
    introducing a bacterial sample into said path at one end thereof; and
    selectively applying an electrical potential along each of said paths for selectively moving a plasmid first along said first path from said bacterial sample to said elution window, then along said second path to said collection window at the end thereof.

18. A purification process according to claim 17 wherein said gel is an electrophoretic agarose gel.

19. A purification apparatus according to claim 17 wherein said gel is an agarose-acrylamide double phase gel.

20. A purification apparatus according to claim 19 wherein said gel has an approximate one percent agarose phase extending from said inlet means part way to said elution window, and an approximate five percent acrylamide phase extending from said agarose phase to said elution window.

* * * * *